(12) United States Patent
Mikkaichi et al.

(10) Patent No.: US 7,988,618 B2
(45) Date of Patent: Aug. 2, 2011

(54) MEDICAL PROCEDURE VIA NATURAL OPENING

(75) Inventors: Takayasu Mikkaichi, Tokyo (JP);
Kensei Nakahashi, Tokyo (JP)

(73) Assignee: Olympus Medical Systems Corp, Tokyo (JP)

( * ) Notice: Subject to any disclaimer, the term of this patent is extended or adjusted under 35 U.S.C. 154(b) by 1065 days.

(21) Appl. No.: 11/329,897

(22) Filed: Jan. 11, 2006

(65) Prior Publication Data
US 2007/0157937 A1   Jul. 12, 2007

(51) Int. Cl.
*A61B 1/00*   (2006.01)
*A61B 5/05*   (2006.01)
*A61B 19/00*   (2006.01)

(52) U.S. Cl. ........ 600/114; 600/104; 600/106; 600/424; 606/130; 128/898

(58) Field of Classification Search .................. 600/114, 600/117, 104, 106, 127, 407, 423, 411, 417, 600/421, 424, 427, 429; 128/899, 898; 606/130
See application file for complete search history.

(56) References Cited

U.S. PATENT DOCUMENTS

| | | | | |
|---|---|---|---|---|
| 5,458,131 A | * | 10/1995 | Wilk | 600/105 |
| 5,681,260 A | * | 10/1997 | Ueda et al. | 600/114 |
| 2004/0050395 A1 | * | 3/2004 | Ueda et al. | 128/899 |
| 2004/0138552 A1 | * | 7/2004 | Harel et al. | 600/407 |

* cited by examiner

*Primary Examiner* — Thomas J Sweet
*Assistant Examiner* — Ryan Henderson
(74) *Attorney, Agent, or Firm* — Scully, Scott, Murphy & Presser, P.C.

(57) ABSTRACT

The medical procedure via a natural opening according to the present invention includes: disposing a target on the body surface near a target site on the inner wall of a hollow organ; introducing a guide member into the hollow organ via a natural natural opening, guiding the guide member to the target site using the target, and confirming the target site by means of a observation device; and carrying out a procedure at the target site while observing the target site.

12 Claims, 15 Drawing Sheets

MEDICAL PROCEDURE VIA NATURAL OPENING

BACKGROUND OF THE INVENTION

1. Field of the Invention

The present invention relates to a medical procedure performed via a natural opening.

2. Description of Related Art

Laparoscopic surgery is a conventionally known technique that has been employed when carrying out a medical procedure such as observation or treatment of the internal organs of the human body. Rather than making a large abdominal incision, laparoscopic surgery provides for the medical procedure to be carried out by making several openings in the abdominal wall, and inserting a laparoscope and surgical instruments such as forceps into these respective openings. This type of surgery offers the benefit of reduced stress on the patient, since only small openings are made in the abdominal wall.

As a method of even further reducing stress on the patient, it has been proposed in recent years to carry out medical procedures by inserting a flexible endoscope into the patient via a natural opening such as the mouth, nostrils or anus. One example of such a medical procedure is disclosed in U.S. Pat. No. 5,458,131.

In this method, a flexible endoscope is inserted via the mouth of the patient. An opening is made in the stomach wall and the end portion of the endoscope is relayed out through this opening into the abdominal cavity. Then, while employing the endoscope as an observation device for the inside of the abdominal cavity, the desired medical procedure is performed within the abdominal cavity using instruments inserted through the endoscope or via another opening.

SUMMARY OF THE INVENTION

An object of the present invention is to provide a method that enables easier confirmation of the target site where a procedure on a hollow organ is to be performed, by using an observation device that has been guided into the hollow organ. The present invention further provides a device for this method.

The medical procedure via a natural opening according to a first aspect of the present invention includes: disposing a target on the body surface near a target site on the inner wall of a hollow organ; introducing a guide member into the hollow organ via a natural opening; guiding the guide member to the target site using the target; confirming the target site by means of the observation device; and carrying out a procedure at the target site while observing the target site.

The medical procedure via a natural opening according to a second aspect of the present invention includes: disposing a target that generates electromagnetic force at the body surface near the incision target site on the inner wall of a hollow organ; introducing a guide member that generates an electromagnetic effect with the target, in the vicinity of the hollow organ, searching for the site where the target is disposed using the electromagnetic effect generated between the target and the guide member, and confirming the position of the incision target site using the observation device that was introduced via a natural opening; and making an incision while observing the incision target site.

DESCRIPTION OF THE PREFERRED EMBODIMENTS

Embodiments according to the present invention will now be explained below. Structural elements that are equivalent in the following discussion will be assigned the same numeric symbol and redundant explanation thereof will be omitted.

First Embodiment

Figure 1:
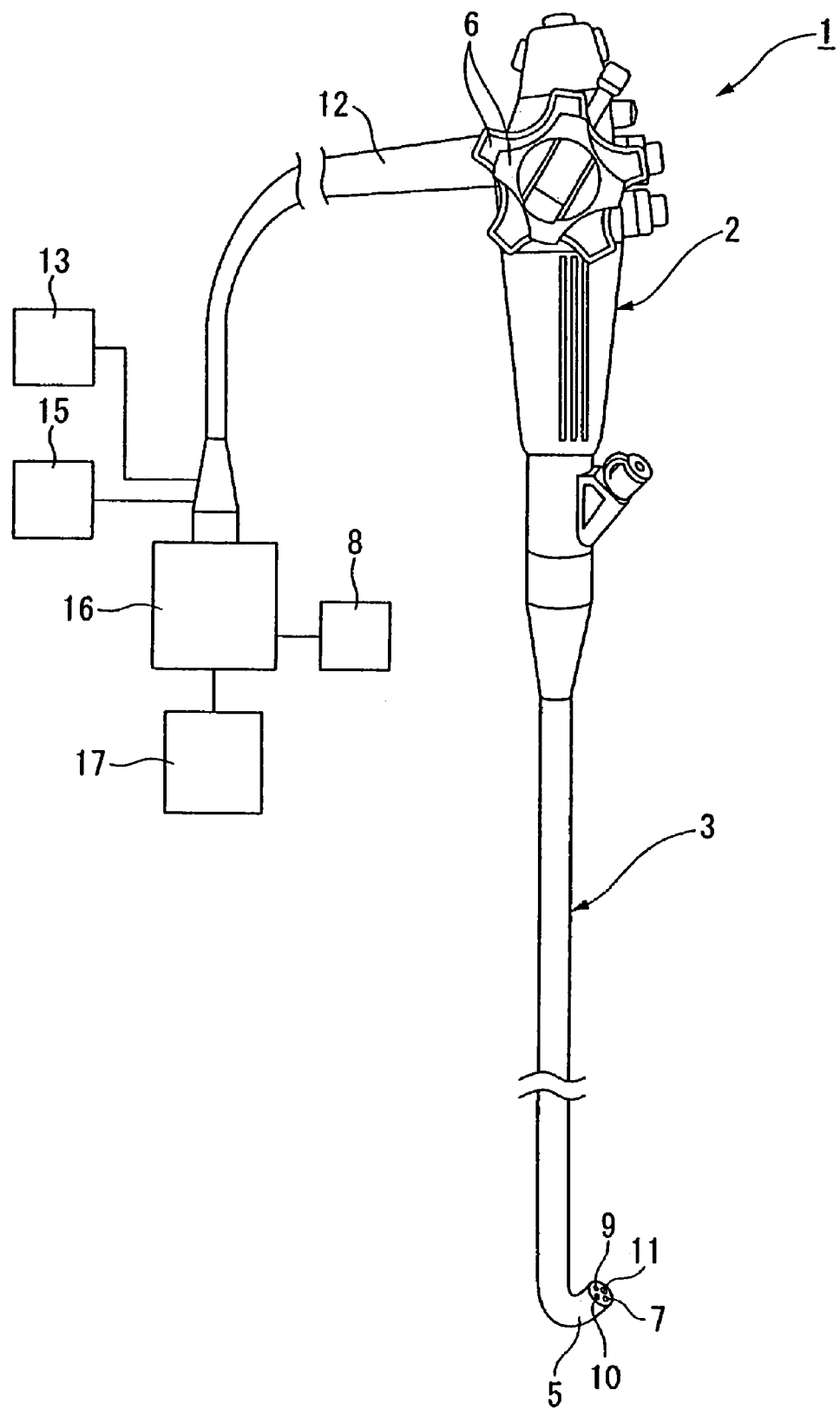
FIG. 1 is a view showing an endoscope employed in the embodiments, as one example of a device used in a medical procedure.

A flexible endoscope 1 is shown in FIG. 1 as an example of a device employed in the present embodiment. The endoscope 1 is provided with an elongated insertion part 3 that extends out from an operation part 2, which is manipulated by the operator. The insertion part 3 has a flexibility, and is inserted into the patient's body. The end 5 of the insertion part 3 can be bent by operating an angle knob 6 that is disposed to the operation part 2. At the end of the insertion part 3 there is disposed a observation device (alternatively referred to as "observation device") 7, composed of an observation optical system such as an objective lens or the like, and a CCD, used as an image pick-up element; an illuminating device 9 composed of an optical fiber for guiding light from a light source device 8 disposed outside the body, and an illuminating optical member for forming the light rays radiated from the end surface of the optical fiber into a desired form; and the end openings for channels 10 and 11. The channel 10 is a conduit that is connected to a gas/water supplying device 13 and a suction device 15 that are disposed outside the body, via a universal cable 12, and that is employed for supplying and evacuating flow to and from the body. The channel 11 is a conduit that is employed for inserting and removing instruments. The observed image that is input to the observation device 7 is displayed on a monitor 17 via a controller 16.

Figure 2:
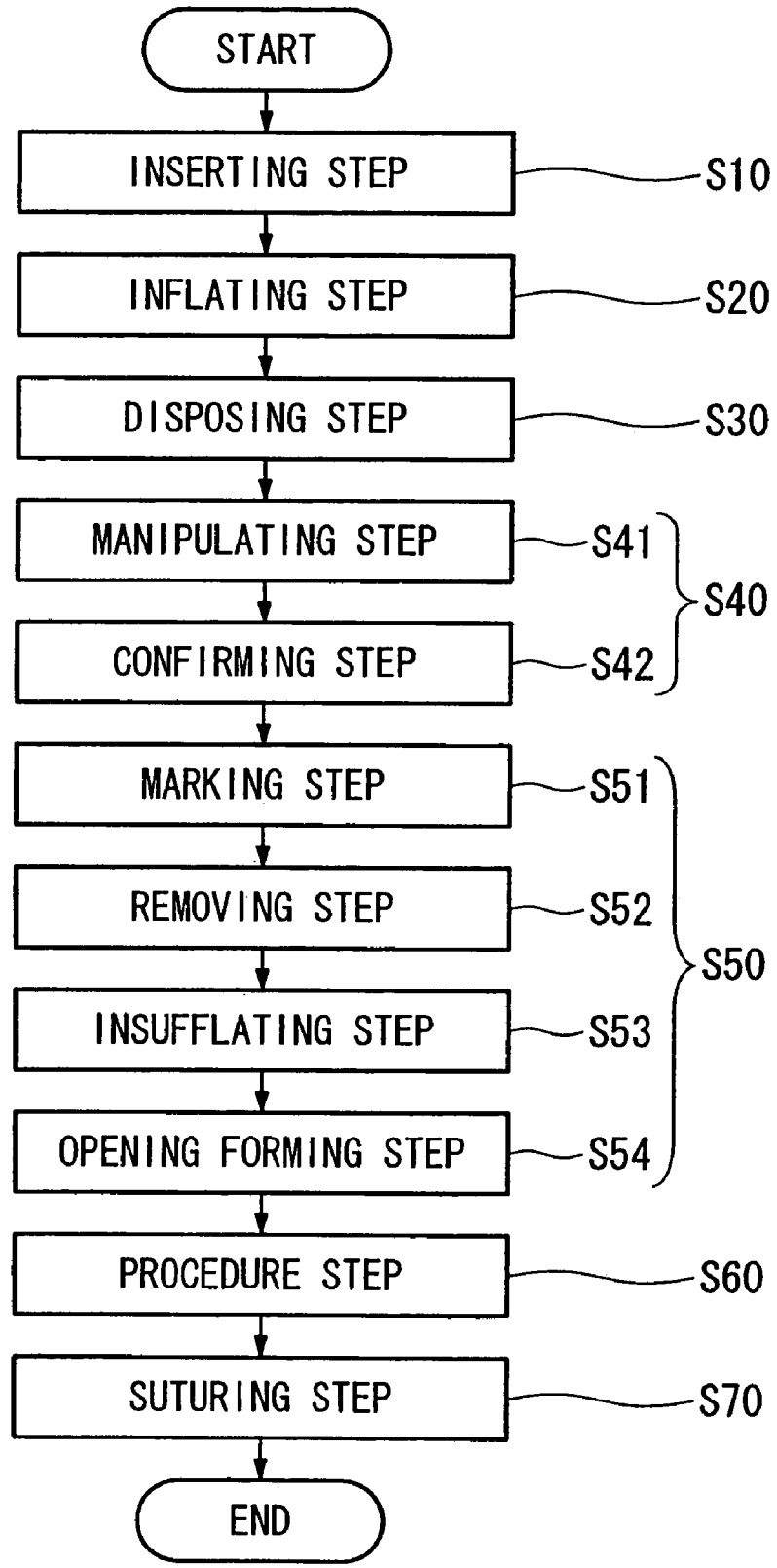
FIG. 2 is a flow diagram showing a medical procedure according to the first embodiment.

The effects of the present embodiment in which this endoscope 1 is employed will be explained following the flow diagram shown in FIG. 2. Note that the following discussion explains a medical procedure in which the endoscope 1 is inserted via the mouth M of a patient PT into the stomach (hollow organ) ST, an opening is formed in the stomach wall, the insertion part 3 of the endoscope 1 is inserted into the abdominal cavity AC, and a medical procedure is performed. Note that in this case, the natural orifice into which the endoscope 1 is inserted is not limited to the mouth M; rather, this explanation is applicable to the nostril, anus, or any other natural opening. With regard to the medical procedure carried out in the abdominal cavity AC, a variety of procedures, such as suturing, observation, incision, resection, cellular sampling or the like, may be carried out alone or in combination.

The patient PT is placed on his/her back, so that the anterior wall of the stomach ST, where a target site T is located, is on top.

Figure 3:
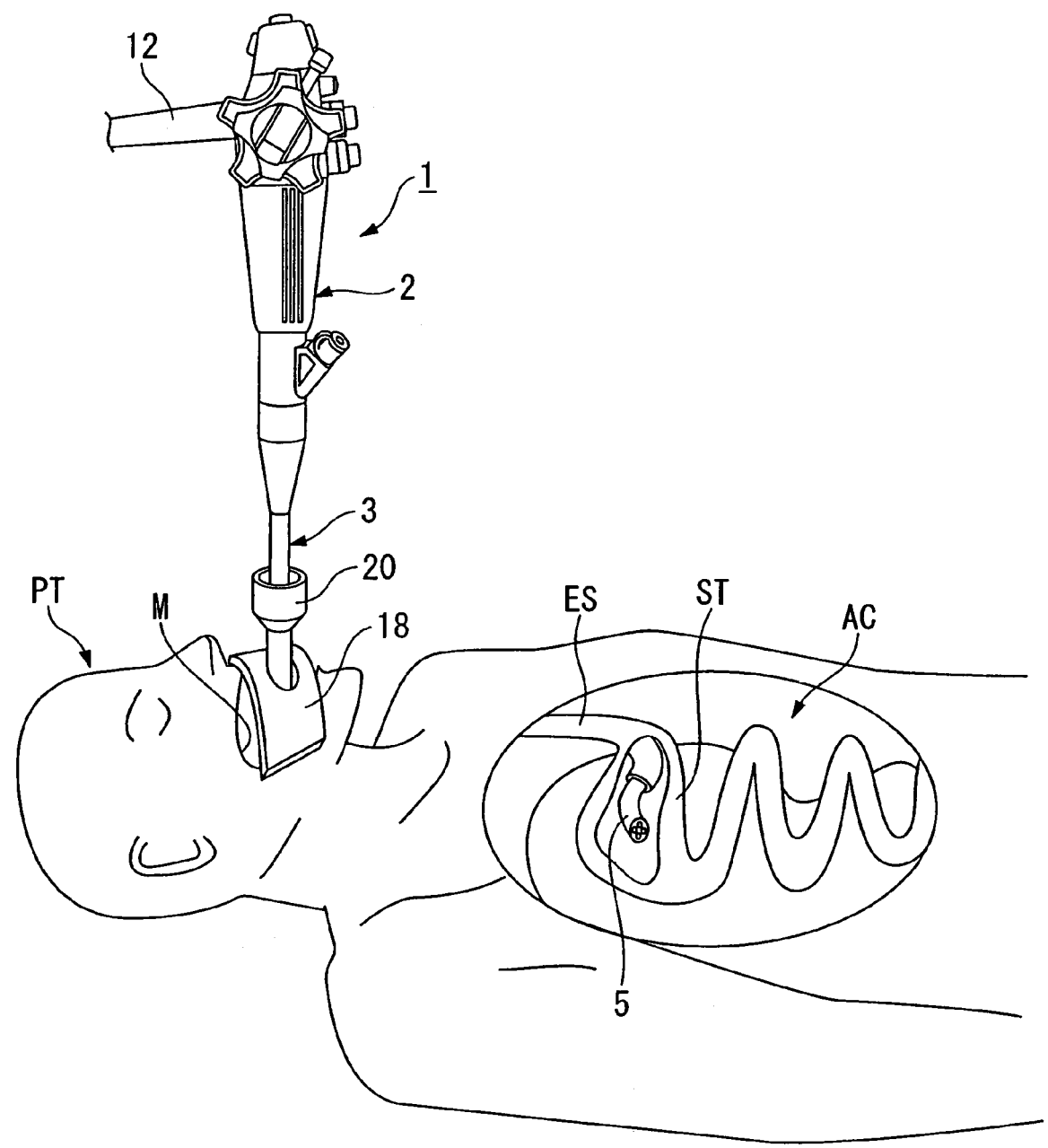
FIG. 3 is a view for explaining the arrangement for inserting the endoscope into the stomach in a medical procedure according to the first embodiment.
Figure 4:
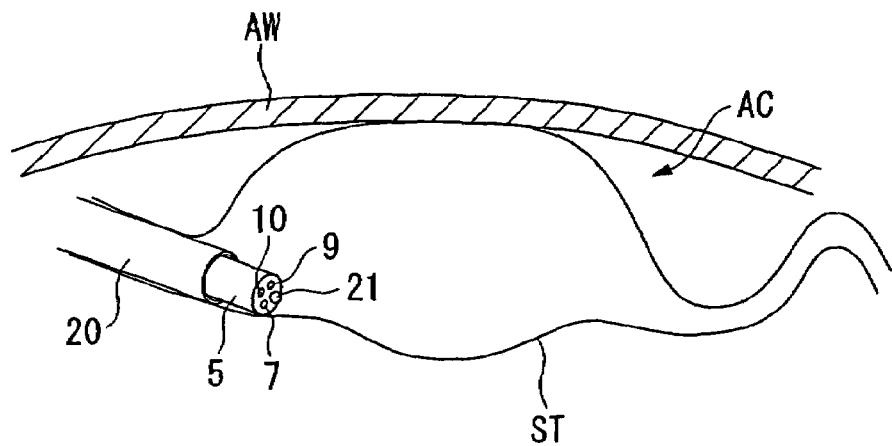
FIG. 4 is a view for explaining the arrangement in which the endoscope has been inserted into the stomach in a medical procedure according to the first embodiment.

Next, inserting step (S10) in which the endoscope 1 is inserted into the stomach ST is carried out. Namely, a mouth piece 18 is attached at the mouth of the patient PT, and the insertion part 3 of the endoscope 1 is inserted via the mouth piece 18 into the esophagus ES. More preferably, the end of the insertion part 3 is inserted into the stomach ST by inserting the endoscope 1 into an over-tube 20, as shown in FIG. 3. The over-tube 20 is employed as an insertion guide tube for inserting the endoscope 1 or other such device that has the insertion part 3, into the body. However, it is also acceptable to directly insert the endoscope 1 without employing the over-tube 20. As shown in FIG. 4, a magnetic body (a guide member formed from a member that generates a magnetic effect with a target, explained further below) 21 is attached to the opening at the end of the channel 10, for example, at the end of the insertion part 3. Note that the magnetic body 21 may be a magnet, or may be equipped with a metal piece.

Next, in inflating step (S20), air from the gas/water supplying device 13 is supplied into the stomach ST via the channel 10 of the insertion part 3, to inflate the stomach ST with air.

Figure 5:
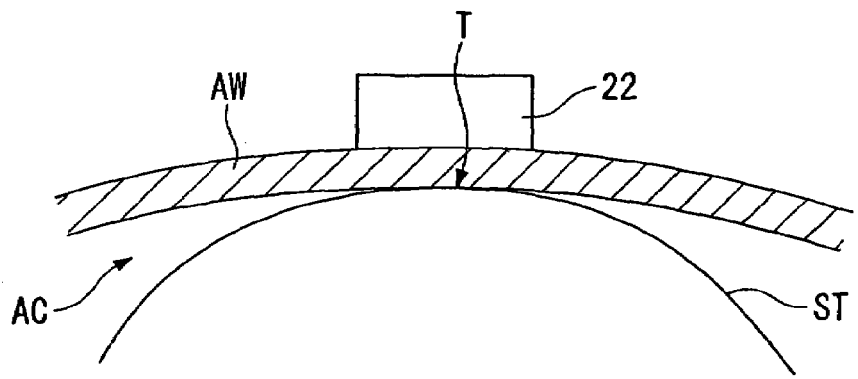
FIG. 5 is a view for explaining the state in which the stomach has been inflated in a medical procedure according to the first embodiment.

Proceeding to disposing step (S30), a magnet (i.e., target for generating magnetic force formed of a member that produces a magnetic effect with the guide member) 22 is adherently disposed in contact with the abdominal wall AW on the outside of the body, as close as possible to the target site T on the stomach wall (i.e., as close as possible to the anterior wall of the stomach ST in the present embodiment), as shown in FIG. 5. Note that it is not absolutely necessary to carry out disposing step (S30) on this timing.

Figure 6:
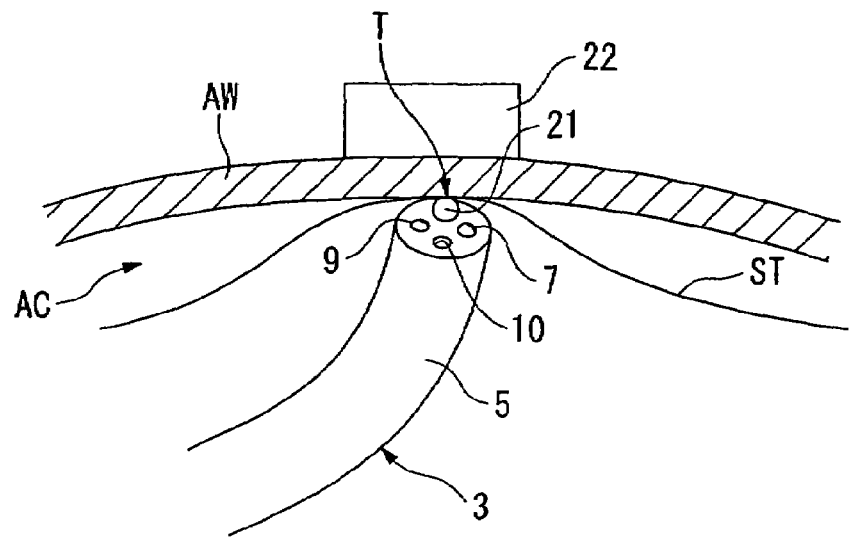
FIG. 6 is a view for explaining the arrangement in which a magnetic body has approached a magnet in a medical procedure according to the first embodiment.

The process then proceeds on to detecting step (S40). In manipulating step (S41), the stomach wall is traced by operating the angle knob 6 to bend and manipulate the end of the insertion part 3 inside the stomach ST. A search is then made from within the stomach ST for the position of the magnet 22 using the attraction from the magnetic force generated between the magnetic body 21 and the magnet 22. As shown in FIG. 6, when the magnetic body (guide member) 21 and the magnet (target) 22 are attracted and draw closer to one another, the end of the insertion part 3 is drawn toward the target site T due to this magnetic force.

In confirming step (S42), the target site T is displayed and confirmed on the monitor 17 via the observation device (observation device) 7.

The process then proceeds to incising step (S50).

First, in marking step (S51), a marking instrument for marking the stomach wall using cautery or the like, is inserted into the channel 11 of the insertion part 3, and a marking is made near the target site T.

Once marking is completed, the magnet 22 which is attached to the abdominal wall AW is removed in the magnet 22 removing step (S52).

Figure 7:
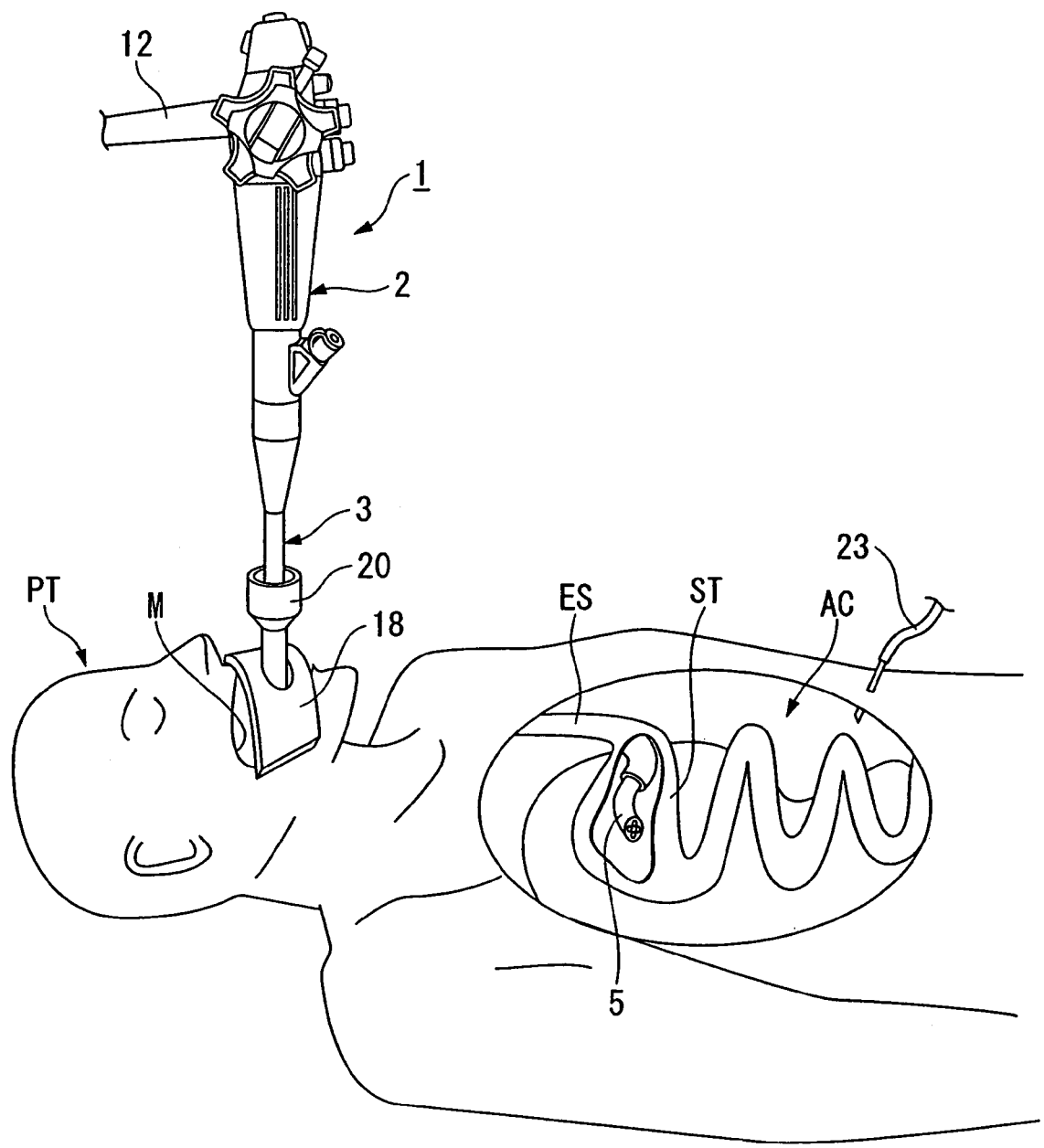
FIG. 7 is a view for explaining the arrangement for an insufflation in a medical procedure according to the first embodiment.

Next, in insufflating step (S53), the end of an insufflation needle 23 is passed from outside the body through the abdominal wall AW, and into the abdominal cavity AC, as shown in FIG. 7, for example. The abdominal cavity AC is then inflated with gas via the insufflation needle 23, to create a space between the stomach wall and the abdominal wail AW. In this embodiment, space between the stomach wall and the abdominal wall AW is secured by insufflating the abdominal cavity AC; however, it is not absolutely essential to carry out a insufflating step. Namely, it is also acceptable to employ conventionally known methods such as the suspension method to secure this space. In addition, it is also acceptable to perform the inflating step in advance of the incising step.

Next, the process proceeds to opening forming step (S54). In this step, the marking instrument disposed inside the channel 11 is removed, and a high frequency knife is passed in its place through the channel 11 to extend out from the end opening. The marked target site T is then incised while observing the target site T on the monitor 17, to form an opening SO in the stomach wall (at a position corresponding to the target site T). Note that a combined use instrument may be employed for the marking instrument and the instrument for forming the opening SO.

Figure 8:
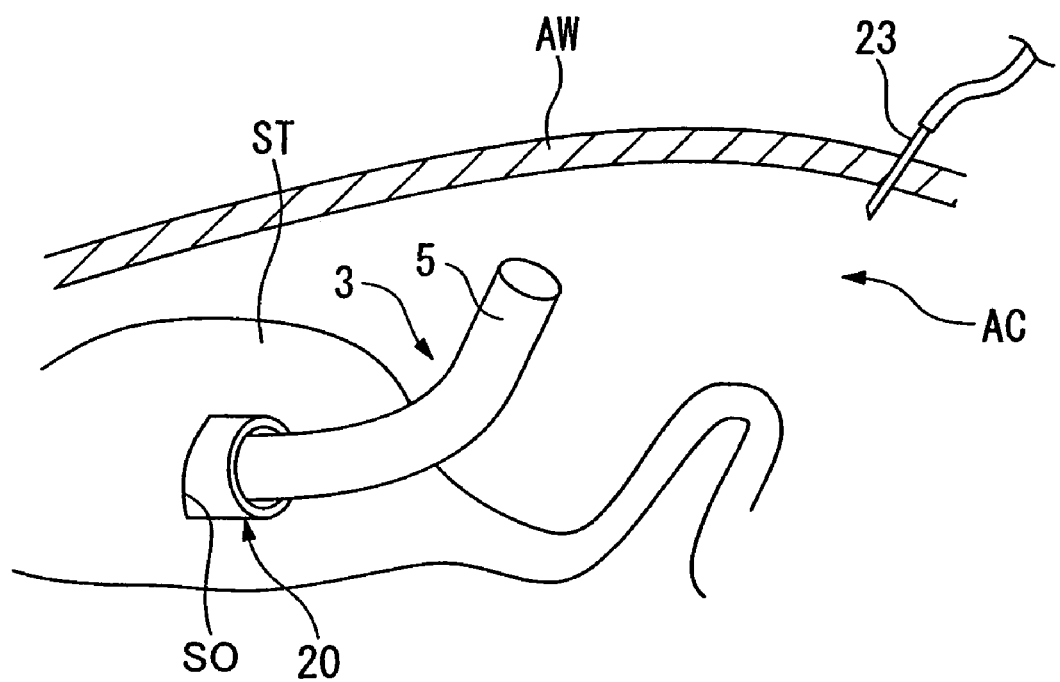
FIG. 8 is a view for explaining the state in which an incision has been made to open the stomach during a medical procedure according to the first embodiment.

After incising, as shown in FIG. 8, the end portion of the insertion part 3 (i.e., the end portion of the insertion part of the device) is projected out into the abdominal cavity AC through the opening SO in the stomach wall, and procedure step (S60) is carried out in which various procedures such as suturing, observation, incising or cell sampling are performed.

Next, the process proceeds to suturing step (S70), in which the opening SO in the stomach wall is sutured closed (the communicating path between the inside of the hollow organ and the abdominal cavity is closed) with a suturing instrument while using the observation device of the endoscope 1 for confirmation.

After suturing, the endoscope 1 is withdrawn from the patient. In the case where the medical procedure was performed by blowing carbon dioxide gas or the like into the abdominal cavity AC in order to secure space with the abdominal cavity, it is desirable to withdraw the insufflation needle 23 after first relieving the pressure within the abdominal cavity AC, and then conclude the medical procedure.

In this embodiment, the target (magnet 22) is disposed after placing the patient PT on his/her back. As a result, the magnet 22 can be disposed under conditions such that the anterior wall of the stomach ST where the target site T is located (i.e., the desired site for incising) is positioned in the upward direction. Further, the magnetic effect generated between the magnetic body (guide member) 21 and magnet (target) 22 serves to draw the magnetic body 21 and the magnet 22 together. As a result, it is possible to identify from within the body where the magnet 22 is located. Further, since the magnet 22 is disposed close to the target site T, it is possible to easily find the target site T on the stomach wall, even in the case where observing from the stomach ST with the endoscope 1. In this case, the magnetic body 21 is disposed to the end of the insertion part 3. As a result, it is possible to observe the target site T, where the insertion part 3 has come to a stop against the stomach wall due to the magnetic force of the magnet 22. In the past, it has been difficult to specify the direction or the location for a procedure (i.e. the location suitable for forming an opening) by means of the endoscope image alone, and practice was required for this procedure. However, in this embodiment, confirmation of the site is facilitated, reducing the burden on the operator.

Since an incision is made in the anterior wall of the stomach ST, it is easy to avoid the greater omentum or other organs when introducing the endoscope 1 into the abdominal cavity AC as a device for carrying out a medical procedure via the opening SO formed by incision in the stomach wall. The endoscope 1 can be readily inserted into the abdominal cavity AC, further facilitating the procedure as a result.

Second Embodiment

A second embodiment will now be explained with reference to the figures.

The difference between the second and first embodiments is that this embodiment employs an instrument 25 having a magnetic body 21 disposed at its end. In this embodiment, in order to insert and remove the instrument 25, it is acceptable to employ an endoscope 28 in which another channel 27 has been provided to an insertion part 26.

Figure 9:
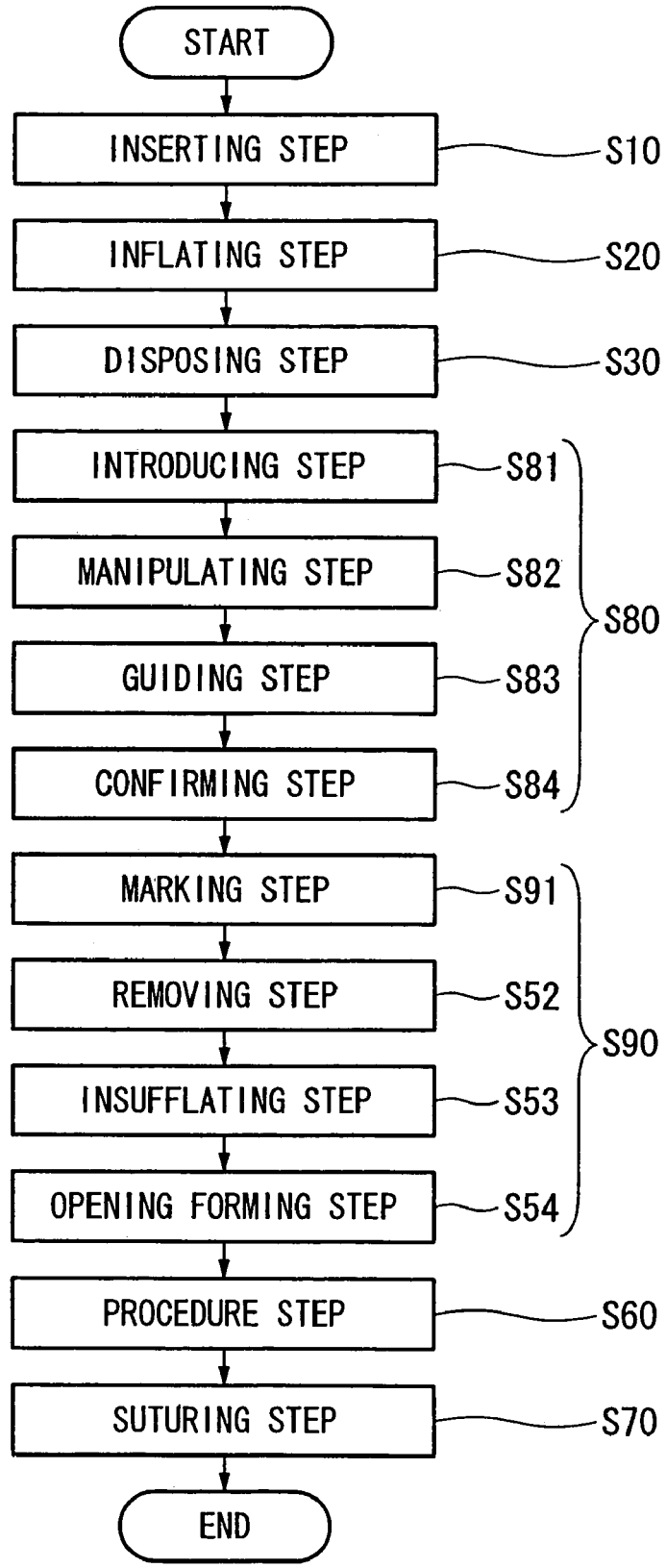
FIG. 9 is a flow diagram showing a medical procedure according to the second embodiment.

The effects of this embodiment will now be explained following the flow in FIG. 9.

First, inserting step (S10), inflating step (S20), and disposing step (S30) are carried out in the same manner as in the first embodiment, and the magnet 22 is disposed as the target to the abdominal wall AW on the outside of the body, as near as possible to the target site T on the stomach wall.

Next, the process proceeds to detecting step (S80). First, in guiding step (S81), the instrument 25 with the magnetic body 21 disposed to the end thereof is inserted into the channel 11, and projected out from the end of the insertion part 26 while grasping the magnetic body 21.

Figure 10:
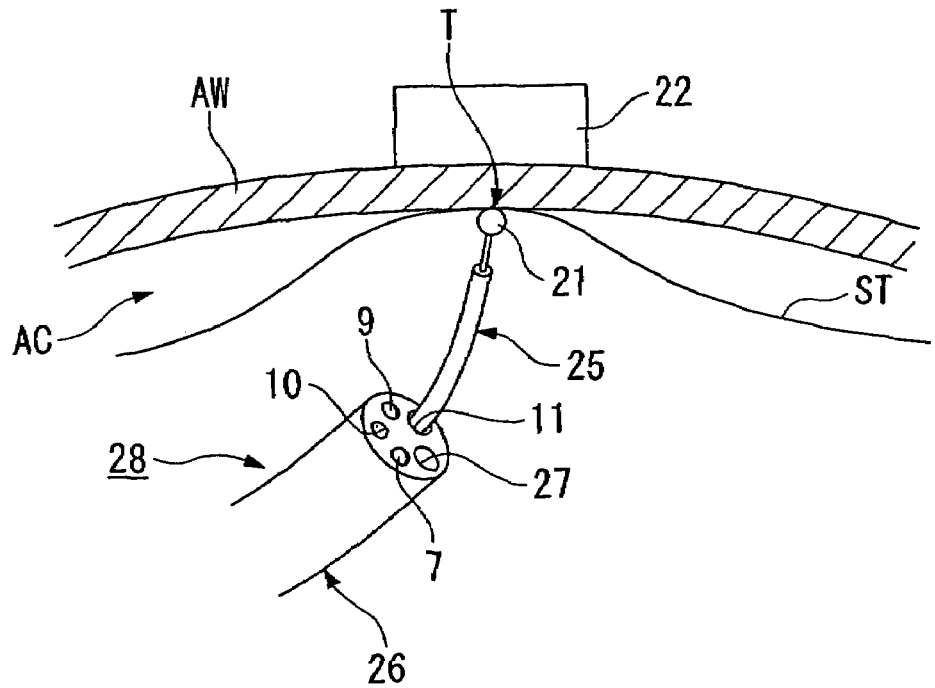
FIG. 10 is a view for explaining the arrangement in which a magnetic body has approached a magnet in a medical procedure according to the second embodiment.

Next, in manipulating step (S82), the stomach wall is traced while bending and manipulating the end of the insertion part 26 inside the stomach ST by manipulating the angle knob 6. A search is made for the attachment site of the magnet 22 from inside the stomach ST using the attraction arising from the magnetic force between the magnetic body 21 and the magnet 22. When the magnetic body 21 is attracted and draws closer to the magnet 22 due to the magnetic force, the end of the instrument 25 is held on the stomach wall in the vicinity of the target site T, as shown in FIG. 10.

Figure 11:
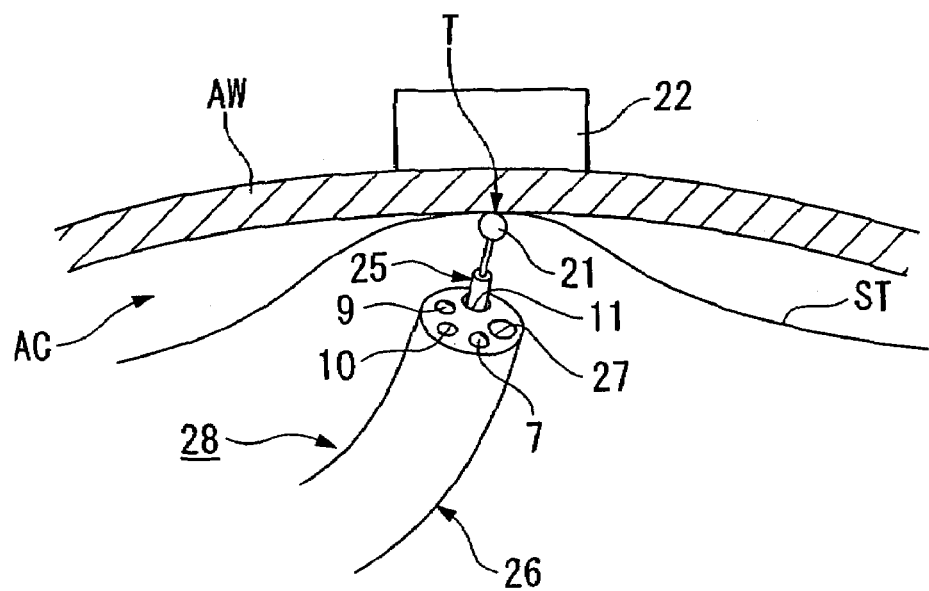
FIG. 11 is a view for explaining the arrangement in which the endoscope is brought close to the target site by employing an instrument as a guide in a medical procedure according to the second embodiment.

Next, in guiding step (S83), with the instrument 25 which is held against the stomach wall employed as a guide, and the insertion part 26 of the endoscope 28 is inserted further into the stomach ST and guided to the magnet 22. As a result, the end of the insertion part 26 is brought closer to the target site T, as shown in FIG. 11.

In confirming step (S84), the image of the target site T is picked up via the observation device (observation device) 7, and the observed image is displayed and confirmed on the monitor 17.

Incising step (S90) is performed next. In marking step (S91), a marking instrument is inserted into the channel 27, which is separate from the channel 11 into which the instrument 25 is inserted, and marking in the vicinity of the target site T is carried out, making it difficult to loose track of the target site.

Once marking is completed, the magnet 22 releasing step (S52), insulating step (S53) and opening forming step (S54) are carried out.

Following incising, procedure step (S60) is carried out. In suturing step (S70), the opening SO in the stomach wall is sutured closed (i.e., the communicating path between the hollow organ and the abdominal cavity is closed), after which the endoscope 28 is withdrawn from the patient. When performing a medical procedure in which carbon dioxide gas or the like is supplied into the abdominal cavity AC in order to secure space within the abdominal cavity AC, it is desirable to withdraw the insufflation needle 23 after first relieving the pressure within the abdominal cavity AC, after which the medical procedure is concluded.

This embodiment provides the same effects as the first embodiment. In particular, the instrument 25 to which the magnetic body 21 is disposed is made to approach the magnet 22. As a result, the end of the insertion part 26 can be brought close to the magnet 22 while ensuring a wider field of vision than in the case where the insertion part 26 of the endoscope 28 is directly manipulated. Further, with the instrument 25 employed as a guide, the insertion part 26 is guided to the target site T, so that the insertion part 26 can be brought closer to the target site T with certainty.

Third Embodiment

The third embodiment will now be explained with reference to the figures.

The third and second embodiment differ with respect to the point that, in this embodiment, marking is carried out by providing high frequency electric current to an instrument 30 which has a magnetic body 21 disposed at its end. The instrument 30 is inserted into the instrument insertion channel (working channel) 11 of the endoscope 1, and is employed to carry out marking. High frequency electric current flows through the instrument 30 by connection to a high frequency power source not shown in the figures.

Figure 12:
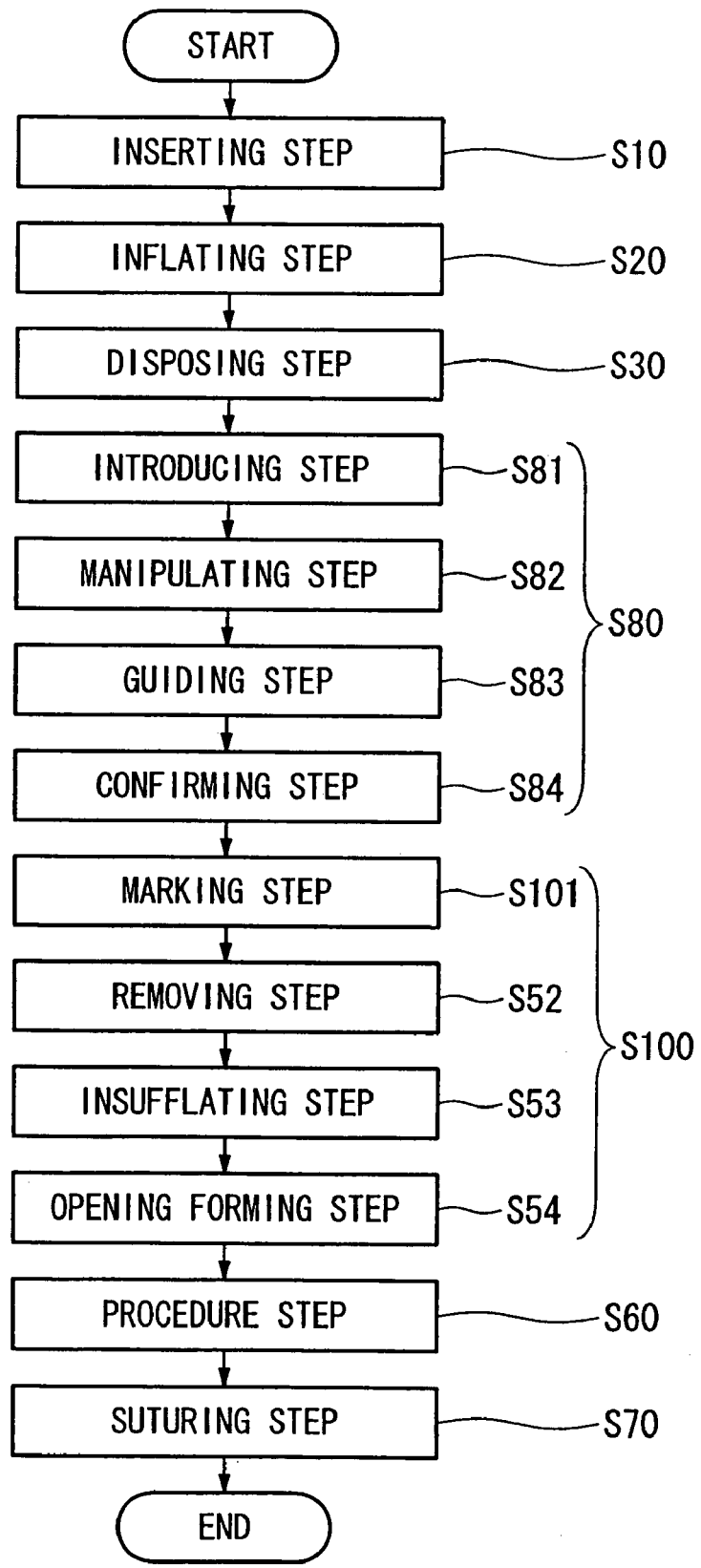
FIG. 12 is a flow diagram showing a medical procedure according to the third embodiment.
Figure 13:
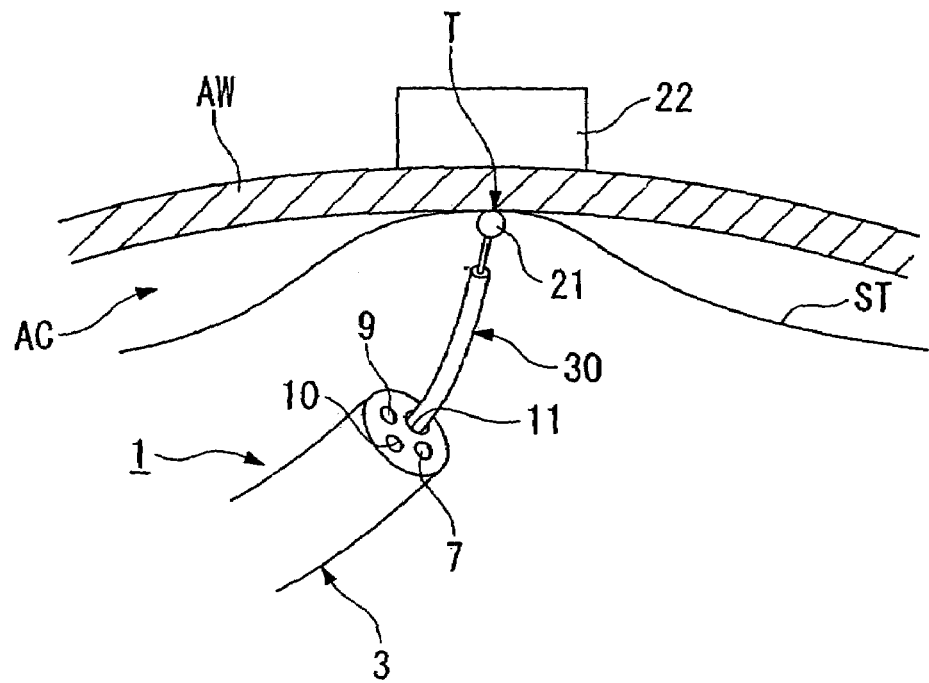
FIG. 13 is a view for explaining the arrangement in which a magnetic body has approached a magnet in a medical procedure according to the third embodiment.

The effects of this embodiment will now be explained following the flow chart in FIG. 12.

Figure 14:
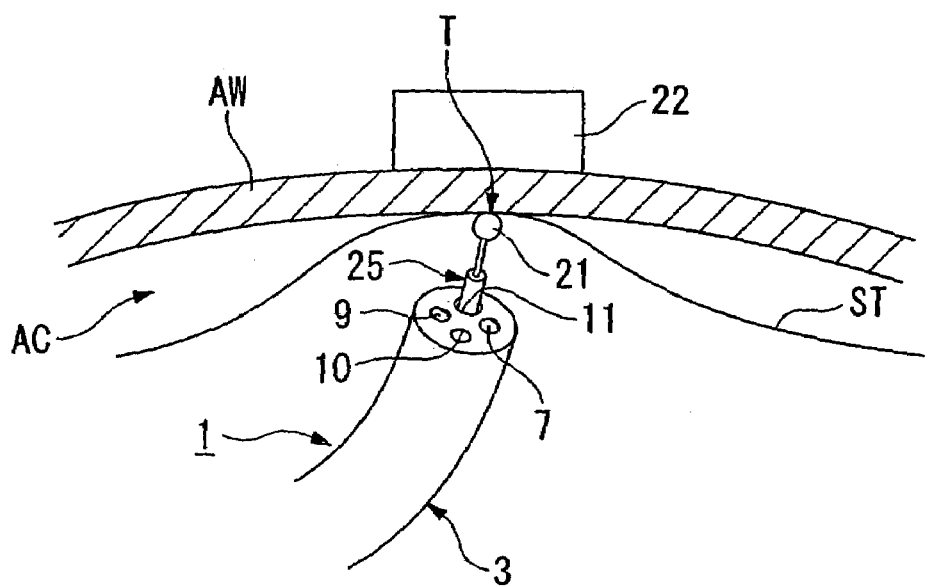
FIG. 14 is a view for explaining the arrangement in which the endoscope is brought close to the target site by employing an instrument as a guide in a medical procedure according to the third embodiment.

First, inserting step (S10), inflating step (S20), and disposing step (S30) are carried out in the same manner as in the second embodiment, and magnet (target) 22 is disposed to the abdominal wall AW on the outside of the body as near as possible to the target site T on the stomach wall. Detecting step (S80) is carried out, after which, with the instrument 30 is employed as a guide, the insertion part 3 of the endoscope 1 is guided to the magnet 22 due to the attraction arising from the magnetic force between magnetic body (guide member) 21 and the magnet 22. As a result, as shown in FIG. 14, the end of the insertion part 3 approaches the vicinity of the target site T and the target site T is confirmed.

Next, the process proceeds to incising step (S100). First, in marking step (S101), the instrument 30 and a high frequency electric source are electrically connected, and the angle knob 6 of the endoscope 1 is operated while observing the target site T on the monitor 17. In this way, the end of the instrument 30 is moved while applying pressure around the target site T. The magnetic body 21 and the magnet 22 are joined by magnetic force due to the magnetic effect generated between them (i.e., the magnetic body 21 is attracted to the magnet 22 by magnetic force). As a result, high frequency electric power is impressed on the instrument 30 from the high frequency power source, carrying out marking around the target site T.

After completion of marking, the magnet 22 removing step (S52), insufflating step (S53), and opening forming step (S54) are performed. After incising, procedure step (S60) is carried out. In suturing step (S70), the opening SO in the stomach wall is sutured closed (i.e., the communicating path between the inside of the hollow organ and the abdominal cavity is closed), and the endoscope 1 is withdrawn from the patient. In the case where an insufflating step (S53) was performed, it is desirable to withdraw the insufflation needle 23 after first relieving the pressure within the abdominal cavity AC, and then conclude the medical procedure.

This embodiment offers the same effects as those of the second embodiment. In particular, since the instrument 30 having the magnetic body 21 disposed at its end is used as is for marking, marking can be carried out with the magnetic body 21 and the magnet 22 in a state of attraction. Further, it is not necessary to exchange or add instruments when marking, so that it is acceptable to have just one instrument insertion channel in the endoscope 1. As a result, a device (the endoscope 1 in this embodiment) that has an insertion part that is narrow in diameter can be employed.

Fourth Embodiment

The fourth embodiment will now be explained with reference to the figures.

The difference between the fourth and second embodiments is that the magnetic body 48 is grasped by a grasping forceps 40 in this embodiment.

Figure 15:
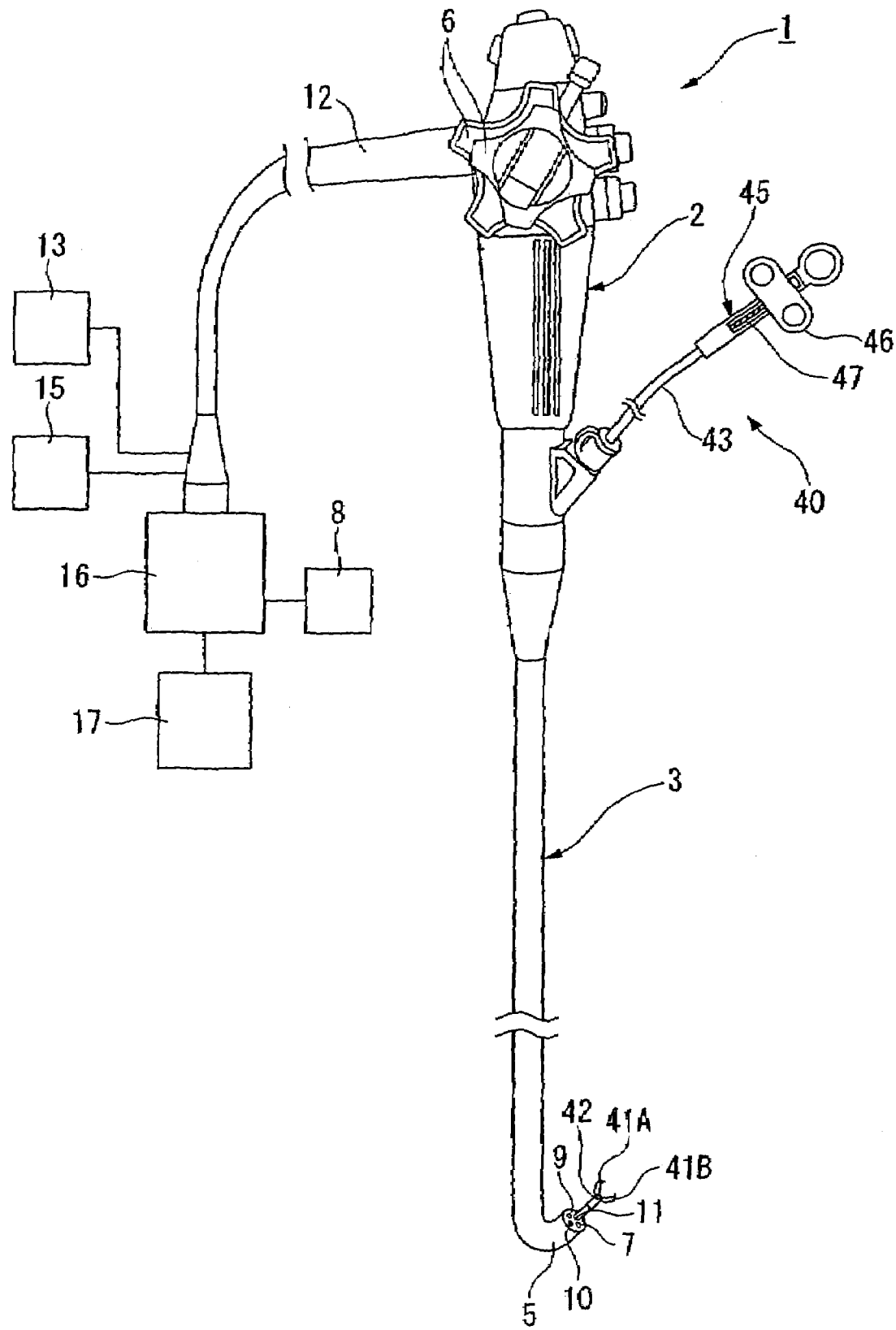
FIG. 15 is a view for explaining the arrangement in which grasping forceps used in a medical procedure according to the fourth embodiment are inserted into the channel of an endoscope.
Figure 16A:
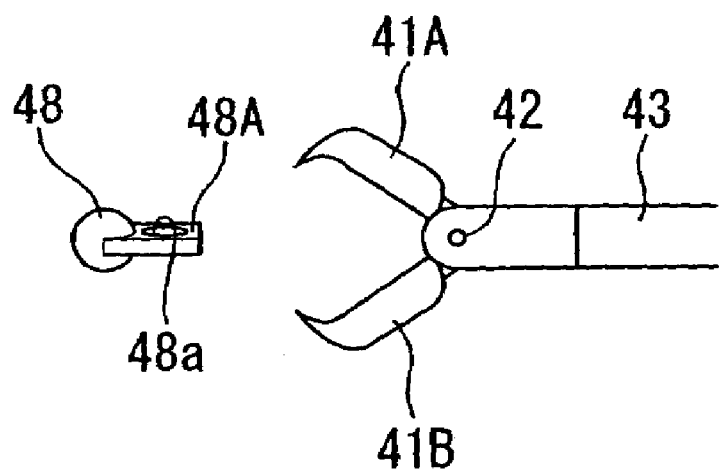
FIG. 16A is a view showing the magnetic body and grasping forceps employed in a medical procedure according to the fourth embodiment.

As shown in FIGS. 15 and 16A, the grasping forceps 40 are provided with paired forceps pieces 41A and 41B which pivot about a pivot axis 42 at the end of the forceps insertion part 3. The pair of forceps pieces 41A and 41B is connected to a wire 47 which is connected to a handle 46. By moving the handle 46 with respect to a forceps operation part 45, which is connected to the base of the forceps insertion part 3, the pair of forceps pieces 41A and 41B are opened and closed by their rotation around the pivot axis 42, due to the forward and reverse operation of the handle 46. The grasping forceps 40 can be freely inserted into or removed from the channel 11 of the insertion part 3 of the endoscope 1.

Figure 16B:
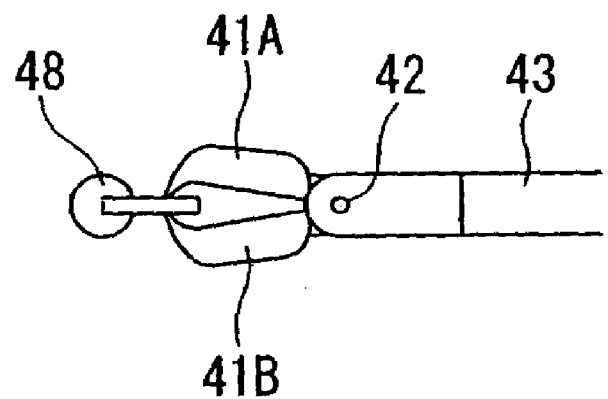
FIG. 16B is a view for explaining the arrangement in which a magnetic body used in a medical procedure according to the fourth embodiment is grasped by grasping forceps.

As shown in FIG. 16B, magnetic body (guide member) 48 has an outer diameter that is roughly the same as the outer diameter of the grasping forceps 40. A grasped member 48A is disposed to the magnetic body 48 so as to enable grasping by, the paired forceps pieces 41A and 41B of the grasping forceps 40. A through hole 48a is formed in grasped part 48A so as to permit passage of the ends of paired forceps pieces 41A and 41B.

Figure 17:
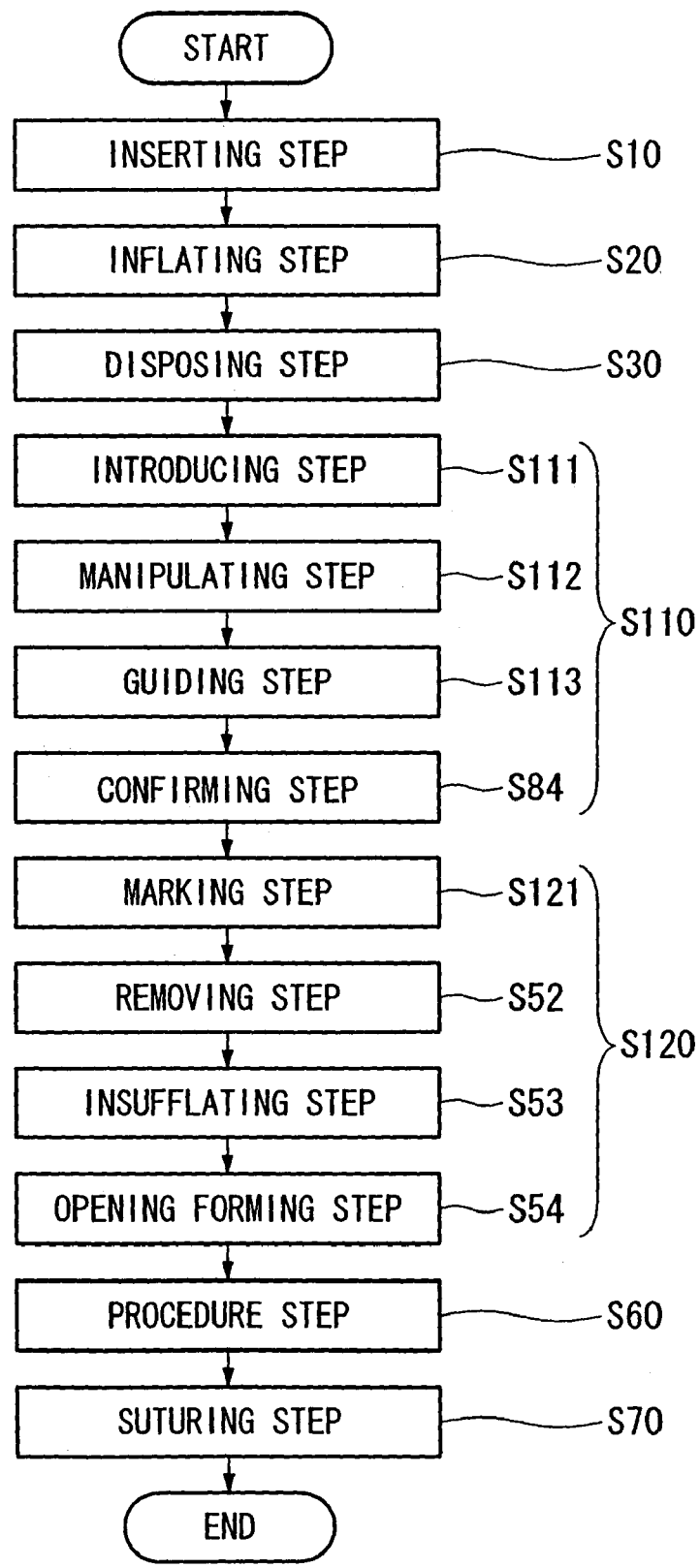
FIG. 17 is a flow diagram showing a medical procedure according to the fourth embodiment.

The effects of this embodiment will now be explained following the flow shown in FIG. 17.

First, as in the second embodiment, inserting step (S10), inflating step (S20) and disposing step (S30) are carried out, and magnet (target) 22 is disposed to the abdominal wall AW on the outside of the body, as close as possible to the target site T on the stomach wall.

Next, the process proceeds to detecting step (S110). In guiding step (S111), the grasping forceps 40, which hold grasped part 48A of the magnetic body 48 in paired forceps pieces 41A and 41B, is inserted into the channel 11 of the endoscope 1, and is projected out from the end of the insertion part 3 while holding grasped part 48A of the magnetic body 48.

Figure 18:
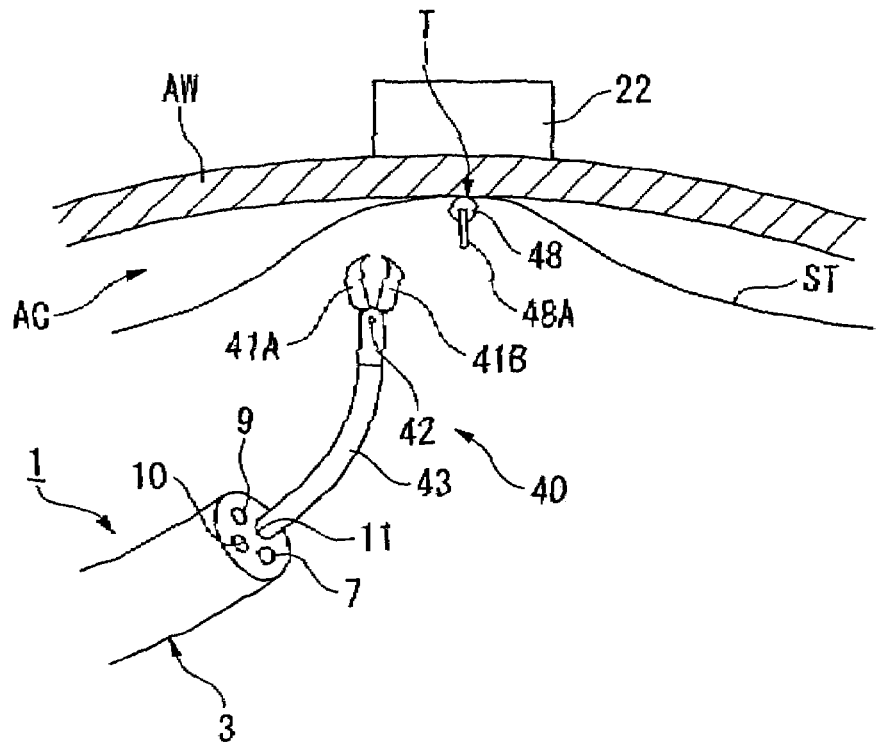
FIG. 18 is a view for explaining the arrangement in which a magnetic body has approached a magnet in a medical procedure according to the fourth embodiment.
Figure 19:
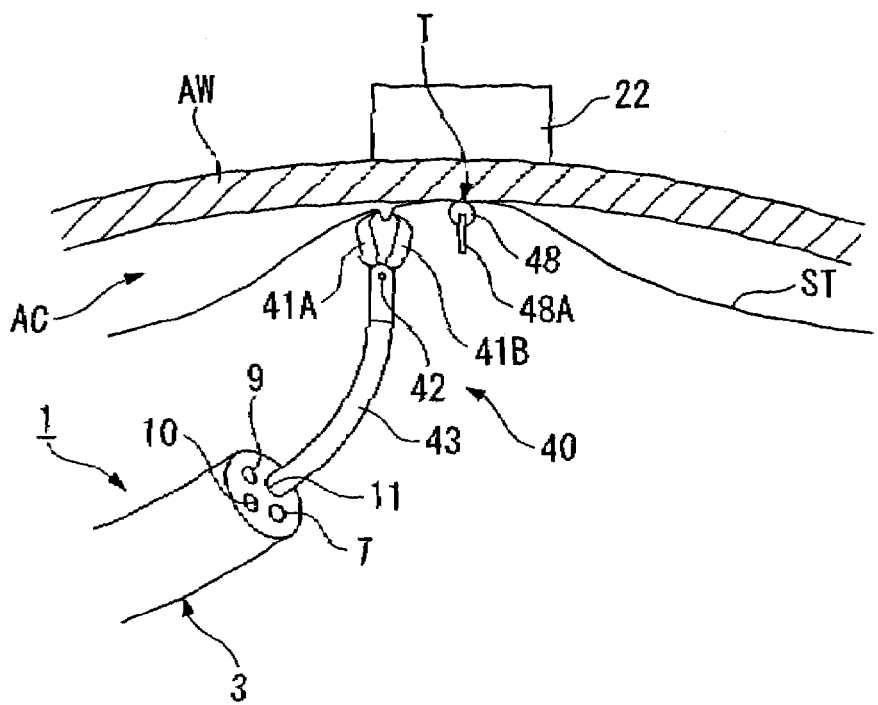
FIG. 19 is a view for explaining the arrangement in which the target site is grasped with grasping forceps while confirming the magnetic body in a medical procedure according to the fourth embodiment.

In manipulating step (S112), the angle knob 6 is used to bend and manipulate the end of the insertion part 3 within the stomach ST to trace the stomach wall in accordance with the attraction generated by the magnetic force between the magnetic body 48 and the magnet 22. In this way, a search from within the stomach ST is made for the attachment position of the magnet 22. Once the magnetic body 48 detects and is attracted to the magnet 22, then, even if paired forceps pieces 41A and 41B of forceps 40 are opened, the magnetic body 48 remains behind, disposed to the stomach wall, due to the magnetic force generated between the magnet 22 and the magnetic body 48, as shown in FIG. 18. Next, as shown in FIG. 19, the end of the grasping forceps 40 is held near the target site T by grasping the tissue in the vicinity of the target site T with the grasping forceps 40.

Figure 20:
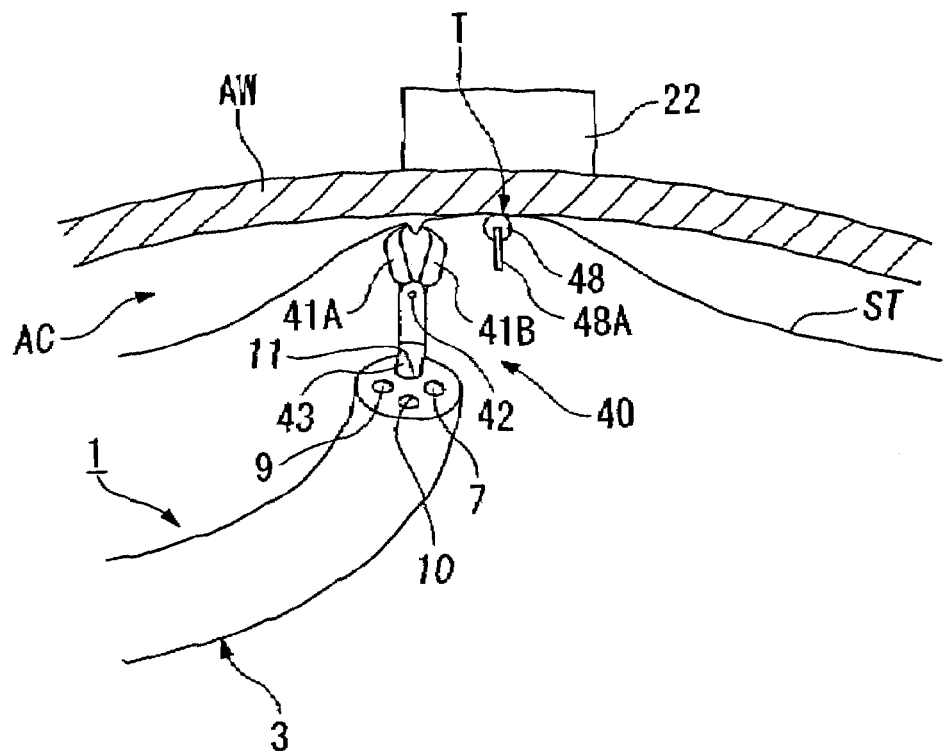
FIG. 20 is a view for explaining the arrangement in which the endoscope is brought close to the target site by employing grasping forceps as a guide in a medical procedure according to the fourth embodiment.

Next, in guiding step (S13), the insertion part 3 of the endoscope 1 is guided to the magnet 22 using the grasping forceps 40 as a guide, with the end of the insertion part 3 brought close to the target site T, as shown in FIG. 20.

Next, confirming step (S84) is carried out in the same manner as in the second embodiment. An image of the target site T is picked up via the observation device (observation device) 7, and the observed image is displayed on the monitor 17 for confirmation.

Figure 21:
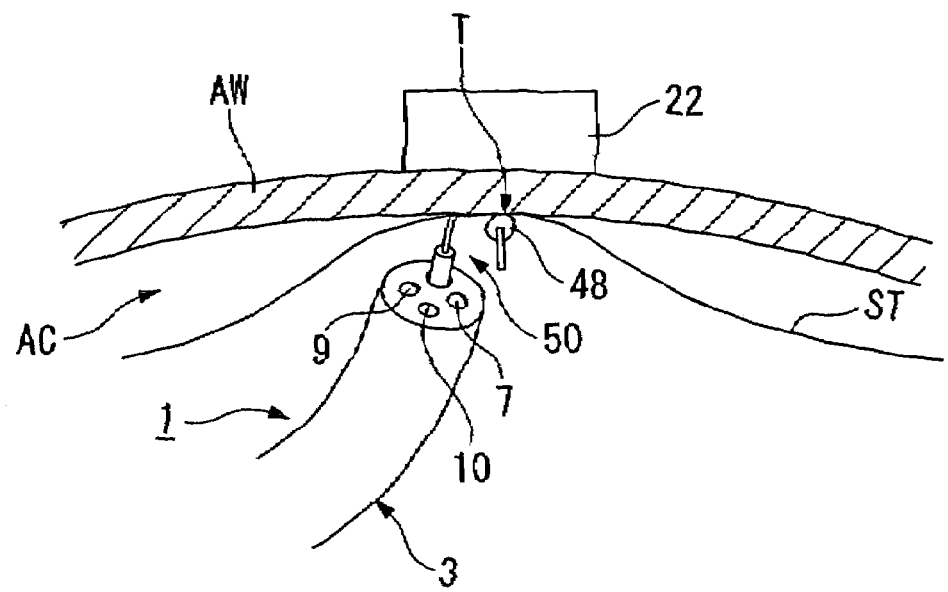
FIG. 21 is a view for explaining the arrangement for marking the stomach wall in a medical procedure according to the fourth embodiment.

Next, the process proceeds to incising step (S120). First, in marking step (S121), the grasping forceps 40 is removed from the channel 11 and marking instrument 50 is inserted into the channel 11 in its place. Marking of the area around the magnetic body 48 is then carried out as shown in FIG. 21.

After marking, the magnet 22 removing step (S52), insufflating step (S53), and opening forming step (S54) are carried out. The magnetic body 48 is also removed from the body. After incising, procedure step (S60) is carried out, followed by suturing closed the opening SO in the stomach wall in suturing step (S70). The endoscope 1 is then withdrawn from the patient's body, the insufflating needle 23 is removed after first relieving the pressure in the abdominal cavity AC, and the medical procedure is terminated.

This embodiment provides the same effects as those offered by the first embodiment. In particular, the grasping forceps 40, which are holding the magnetic body 48, are drawn toward the magnet 22. As a result, after releasing the magnet 22, the grasping forceps 40 can be used without modification for guiding and in other procedures.

Note that the scope of the present invention is not limited to the preceding embodiments. Rather, it is acceptable to add a variety of modifications provided that they are within limits that do not depart from the spirit of the present invention.

For example, both the target and the guide member were employed as magnets in the preceding embodiment. However, it is also acceptable if either of these were provided as a magnetic body made of iron, for example. Further, an electromagnet may be employed in place of the magnet. In addition, the electromagnetic force is not limited to magnetic force. For example, a metal detector may be employed for the target and metal may be employed as the guide member, and the electromagnetic action of the metal detector may be utilized. Furthermore, the sequence of the steps is not limited to that set forth in these embodiments. Rather, a sequence is acceptable in which a guide member inserted into the hollow organ is employed to search for a target that is disposed to the abdomen on the body surface side (i.e., to search for a target with the guide member).

Further, it is also acceptable to carry out the same procedure while observing inside the body with a wireless-type observation device, by employing a device that has a observation device of the type that wirelessly sends images picked up by a device that can be retained in the body, such as the conventionally known capsule endoscope, to an image display outside the body, and an insertion part that does not have a observation function.

Further, a high frequency instrument was employed as the method for carrying out marking in each of these embodiments. However, the present invention is not limited thereto. Rather, it is also acceptable to carry out marking of the tissue using a clip, needle or the like.

What is claimed is:

1. A medical procedure via a natural opening, for treating a target site located on an inside of a wall of a hollow organ of a patient, the medical procedure comprising:
    disposing a target on an external body surface located directly behind the wall of the hollow organ with respect to the target site such that the wall of the hollow organ is sandwiched between the target and the target site;
    introducing an insertion portion of an endoscope into the hollow organ via a natural opening of the patient's body;
    introducing a guide member and an instrument whose distal end is provided with the guide member into said hollow organ through a channel of the insertion portion of the endoscope previously introduced into the hollow organ;
    bringing the guide member of the instrument towards the target site by using a magnetic force acting between said target and said guide member;
    sandwiching the wall of the hollow organ and the target site between the target and the guide member;
    guiding the insertion portion of the endoscope along the instrument so that a distal end of the insertion portion approaches the target site;
    acknowledging the target site using an observation device disposed on a distal end of said insertion portion of said endoscope; and
    carrying out a procedure at the target site while observing the target site using said observation device.

2. A medical procedure via a natural opening according to claim 1, wherein a magnet or electromagnet is employed as said target.

3. A medical procedure via a natural opening according to claim 2, wherein a magnetic body is employed as said guide member.

4. A medical procedure via a natural opening according to claim 1, wherein disposing said target comprises disposing said target to the body surface on the abdomen that corresponds to the anterior wall of the stomach.

5. A medical procedure via a natural opening according to claim 4, further comprising inflating said hollow organ prior to bringing said guide member towards said target site, using a conduit introduced into said hollow organ via a natural opening.

6. A medical procedure via a natural opening according to claim 2, further comprising:
    introducing into said hollow organ via a natural opening a device in which said observation device and said guide member are disposed to an insertion part provided with a bending part that performs bending operations in response to manipulations by the operator; wherein
    said acknowledging comprises searching for the position of said target by bending said bending part.

7. A medical procedure via a natural opening according to claim 2, further comprising:
    introducing into said hollow organ via a natural opening a device in which said observation device and a channel are disposed to an insertion part provided with a bending part that performs bending operations in response to manipulations by the operator; wherein
    said acknowledging comprises:
    introducing said guide member into said hollow organ via said channel, and
    searching for the position of said target by carrying out at least one of a relative movement of said guide member with respect to said insertion part and a bending operating of said bending part.

8. A medical procedure via a natural opening according to claim 4, wherein carrying out the procedure at said target site comprises incising said target site to form an opening communicating with the abdominal cavity.

9. A medical procedure via a natural opening according to claim 8, further comprising:
    marking said target site which has been confirmed using said observation device; and
    introducing the end of an insufflation conduit into the abdominal cavity either percutaneously or via a natural opening, prior to forming said opening, and insufflating said abdominal cavity in order to form a space between the stomach wall and the abdominal wall.

10. A medical procedure via a natural opening according to claim 8, further comprising:
    inserting a procedure device into said abdominal cavity via said opening and performing the desired procedure within said abdominal cavity using said device;
    withdrawing said device back into said hollow organ after completing the desired procedure within said abdominal cavity; and
    closing the communication between said hollow organ and said abdominal cavity via said opening.

11. A medical procedure via a natural opening according to claim 1, wherein said procedure at said target site includes incising said hollow organ near the target site.

12. The medical procedure according to claim 1, wherein the guide member is integrally formed on the distal end of the instrument.

* * * * *